(12) United States Patent
Ustav, Sr. et al.

(10) Patent No.: US 11,000,529 B2
(45) Date of Patent: May 11, 2021

(54) HUMAN PAPILLOMA VIRUS REPLICATION INHIBITORS

(71) Applicant: Icosagen Cell Factory OÜ, Tartumaa (EE)

(72) Inventors: Mart Ustav, Sr., Õssu (EE); Ene Ustav, Õssu (EE); Andres Männik, Õssu (EE); Mart Toots, Õssu (EE); Andres Tover, Õssu (EE)

(73) Assignee: Icosagen Cell Factory OÜ, Õssu (EE)

(*) Notice: Subject to any disclaimer, the term of this patent is extended or adjusted under 35 U.S.C. 154(b) by 0 days.

(21) Appl. No.: 16/568,310

(22) Filed: Sep. 12, 2019

(65) Prior Publication Data

US 2020/0046730 A1    Feb. 13, 2020

Related U.S. Application Data

(62) Division of application No. 15/573,362, filed as application No. PCT/EP2016/060584 on May 11, 2016, now Pat. No. 10,543,218.

(60) Provisional application No. 62/159,572, filed on May 11, 2015.

(51) Int. Cl.
| | | |
|---|---|---|
| A61K 31/566 | (2006.01) |
| A61K 31/52 | (2006.01) |
| A61K 31/568 | (2006.01) |
| A61K 31/341 | (2006.01) |
| A61K 31/4184 | (2006.01) |
| A61K 31/517 | (2006.01) |
| A61K 31/496 | (2006.01) |
| A61K 31/57 | (2006.01) |
| A61K 31/575 | (2006.01) |
| A61P 31/20 | (2006.01) |
| A61K 31/58 | (2006.01) |

(52) U.S. Cl.
CPC .......... *A61K 31/566* (2013.01); *A61K 31/341* (2013.01); *A61K 31/4184* (2013.01); *A61K 31/496* (2013.01); *A61K 31/517* (2013.01); *A61K 31/52* (2013.01); *A61K 31/568* (2013.01); *A61K 31/57* (2013.01); *A61K 31/575* (2013.01); *A61K 31/58* (2013.01); *A61P 31/20* (2018.01)

(58) Field of Classification Search
CPC ..... A61K 31/566; A61K 31/52; A61K 31/568
See application file for complete search history.

(56) References Cited

PUBLICATIONS

Ratmeyer et al. Biochemistry, 1996, vol., 35, pp. 13689-13696.*

\* cited by examiner

*Primary Examiner* — Samira J Jean-Louis

(74) *Attorney, Agent, or Firm* — Meunier Carlin & Curfman LLC

(57) ABSTRACT

Methods for treating high risk HPV infection by inhibiting one or more phases of HPV replication cycle with antiviral compounds are disclosed. Moreover, a mechanism for the inhibition is suggested and targets for further antiviral compounds are disclosed.

8 Claims, 6 Drawing Sheets

Specification includes a Sequence Listing.

SEQUENCE LISTING

<160> NUMBER OF SEQ ID NOS: 8

<210> SEQ ID NO 1
<211> LENGTH: 46
<212> TYPE: DNA
<213> ORGANISM: artificial sequence
<220> FEATURE:
<223> OTHER INFORMATION: chemically synthesized
<220> FEATURE:
<221> NAME/KEY: misc_feature
<222> LOCATION: (1)..(46)
<223> OTHER INFORMATION: tdp1 shRNA

<400> SEQUENCE: 1
gcacgatctc tctgaaacaa actcgagttt gtttcagaga gatcgt          46

<210> SEQ ID NO 2
<211> LENGTH: 47
<212> TYPE: DNA
<213> ORGANISM: artificial sequence
<220> FEATURE:
<223> OTHER INFORMATION: chemically synthesized
<220> FEATURE:
<221> NAME/KEY: misc_feature
<222> LOCATION: (1)..(47)
<223> OTHER INFORMATION: PARP1 sh-RNA

<400> SEQUENCE: 2
ggactcgctc cggatggcct tcaagagagg ccatccggag cgagtcc         47

<210> SEQ ID NO 3
<211> LENGTH: 27
<212> TYPE: DNA
<213> ORGANISM: artificial sequence
<220> FEATURE:
<223> OTHER INFORMATION: chemically synthesized
<220> FEATURE:
<221> NAME/KEY: misc_feature
<223> OTHER INFORMATION: primer

<400> SEQUENCE: 3
agcatgcaga cacatcagga atattag                              27

<210> SEQ ID NO 4
<211> LENGTH: 27
<212> TYPE: DNA
<213> ORGANISM: artificial sequence
<220> FEATURE:
<223> OTHER INFORMATION: chemically synthesized
<220> FEATURE:
<221> NAME/KEY: misc_feature
<222> LOCATION: (1)..(27)
<223> OTHER INFORMATION: primer

<400> SEQUENCE: 4
gtgccgattg ggtggttgca ggatttg                              27

<210> SEQ ID NO 5
<211> LENGTH: 20
<212> TYPE: DNA
<213> ORGANISM: artificial sequence
<220> FEATURE:
<223> OTHER INFORMATION: chemcially synthesized
<220> FEATURE:
<221> NAME/KEY: misc_feature
<222> LOCATION: (1)..(20)
<223> OTHER INFORMATION: primer

<400> SEQUENCE: 5

```
ggttgcagga actgtgaggt                                                    20

<210> SEQ ID NO 6
<211> LENGTH: 22
<212> TYPE: DNA
<213> ORGANISM: artificial sequence
<220> FEATURE:
<223> OTHER INFORMATION: chemically synthesized
<220> FEATURE:
<221> NAME/KEY: misc_feature
<222> LOCATION: (1)..(22)
<223> OTHER INFORMATION: primer

<400> SEQUENCE: 6
tccgcgacag tcggggcaca gg                                                 22

<210> SEQ ID NO 7
<211> LENGTH: 20
<212> TYPE: DNA
<213> ORGANISM: artificial sequence
<220> FEATURE:
<223> OTHER INFORMATION: chemically  synthesized
<220> FEATURE:
<221> NAME/KEY: misc_feature
<222> LOCATION: (1)..(20)
<223> OTHER INFORMATION: primer

<400> SEQUENCE: 7
gcggcgttat tcccatgacc                                                    20

<210> SEQ ID NO 8
<211> LENGTH: 20
<212> TYPE: DNA
<213> ORGANISM: artificial sequence
<220> FEATURE:
<223> OTHER INFORMATION: chemically synthesized
<220> FEATURE:
<221> NAME/KEY: misc_feature
<222> LOCATION: (1)..(20)
<223> OTHER INFORMATION: primer

<400> SEQUENCE: 8
ggtgcccttc cgtcaattcc                                                    20
```

HUMAN PAPILLOMA VIRUS REPLICATION INHIBITORS

PRIORITY

This application is a divisional application of U.S. application Ser. No. 15/573,362, filed on Nov. 10, 2017, which is a National Stage Entry of PCT/EP2016/060584, filed on May 11, 2016, which claims benefit of U.S. provisional application 62/159,572, filed on May 11, 2015, the contents of all of which are incorporated herein by reference.

SEQUENCE LISTING

This application contains sequence listing that is provided in computer readable form that is identical to the written sequence listing provided.

FIELD OF THE INVENTION

This invention is related generally to the area of inhibiting viral replication. More specifically this invention is related to novel inhibitors of Human Papilloma Virus. Furthermore, the invention is related to identifying target molecules for further antiviral compounds.

BACKGROUND OF THE INVENTION

Human Papillomaviruses (HPVs) infect epithelial tissues of skin and mucosa. HPVs are small double-stranded DNA viruses which cause benign and malignant lesions in the epithelia. Infections are usually cleared by the immune system, however they can become persistent and eventually may develop into various cancers. To date, at least 205 different HPV types have been described, 12 of them (types 16, 18, 31, 33, 35, 39, 45, 51, 52, 56, 58, 59) have been classified as Class 1A carcinogens, also termed as High-risk (HR) HPVs. Types 16 and 18 are most prevalent. Most common cancer associated with HPVs is the cervical cancer: ~500 000 new cases per year mostly in developing countries, and 266 000 deaths were reported in 2008. Moreover, HPV16 and HPV18, have been found to be associated with about 70 invasive carcinomas of the uterine cervix. as well as cancers of the oropharynx, anus. and other mucosal tissues. Low-risk HPVs on the other hand are not usually connected with malignancy.

Current therapies to remove lesions caused by HPVs include various cytodestructive procedures and immuno-modulatory molecules, for example imiquimod. Imiquimod is not specific for HPV, but is used to treat various skin diseases, including skin cancer, melanoma, *molluscum contagiosum* and others. In addition, there are three vaccines available against HPVs: Gardasil (types 6, 11, 16 and 18), Gardasil 9 (types 16, 18, 31, 33, 45, 52, 58, 6 and 11) and Cevarix (types 16 and 18). The main active components in of these vaccines are the L1 capsid proteins of HPV viruses. Moreover, these vaccines are only prophylactic and in addition to this the availability of the vaccines is limited.

HPVs encode two main oncoproteins, E6 and E7, which modify cellular environment to be more suitable for HPV replication by inducing DNA synthesis and cell transformation. E6 and E7 have crucial roles in HPV-related cancer development.

The life cycle of HPVs is strictly dependent on cellular differentiation program. Infection starts by virus entry into undifferentiated basal epithelial cells (possibly stem cells) through micro-wounds. Infection is established by initiating initial amplification during which viral copy number reaches up to few hundred copies per cell. Stable maintenance phase is next, during this stage HPV genome replicates approximately once per cell cycle the viral copy number is constant. Viral gene expression is kept at very low levels. Vegetative amplification and assembly of the virions takes place in highly differentiated cells. To replicate its genome, HPVs largely depend on cellular proteins. They themselves only encode two replication proteins: E1 and E2. E1 is an ATP-dependent DNA helicase, which initiates replication from the non-coding region of HPV genome—URR (LCR). It also interacts with various cellular replication proteins to facilitate viral replication, for example Topoisomerase I, Replication Protein A (RPA) and Polymerase Alpha. For replication, E2 protein forms a complex with E1 and directs it to the replication origin. In addition, E2 is involved in regulation of viral gene expression, and it tethers HPV genomes to mitotic chromosomes for efficient segregation.

Cellular DNA is constantly attacked by exogenous or endogenous DNA-damaging agents such as UV-wavelengths or errors in replication. To cope with it, cells have very sophisticated ways to ensure integrity of DNA, to avoid potential mutations and tumorigenesis: DNA damage response network (DDR). DDR network is orchestrated by different kinases (ATM, ATR and DNA-PK) and damage in DNA is repaired by two major pathways: Homologous recombination (HR) and Non-homologous end-joining (NHEJ). In recent years it has become clear that many viruses are not only capable of activating DDR but they also benefit from its activation. HPV genomes are replicated in distinct foci in the cell's nucleus which contain cellular proteins necessary in DDR. By activating DDR, HPVs recruit replication proteins to these foci which in turn help to efficiently replicate viral genomes. HPV replication machinery uses Homologous recombination dependent replication during amplification of viral genome which results in accumulation of oligomerized molecules containing at least two genomes.

Important proteins in DDR network are Tyrosyl-DNA-phosphodiesterases Tdp1 and Tdp2 as well as PARP1(poly-(ADP-ribose)-polymerase 1). Topoisomerases as part of Top1/Top2 cleaving complex (Top1/2cc) are proteins that locally relax otherwise tightly packed nucleic acids which is required for replication and transcription. Several exogenous and endogenous DNA damaging agents, however cause entrapment of Top1/2cc-s. Entrapped cleaving complexes cause DNA breaks due to the collision of replication forks. Tdp1 is a key enzyme in repairing DNA damage caused by Top1 cc-s. It hydrolyzes phosphodiester bond between Top1 and DNA, thereby releasing Top1cc. PARP1 (Poly(ADP-ribose) polymerase-1) is an enzyme that binds to DNA and catalyzes addition of ADP-ribose polymers (PAR) to its target proteins. These modifications regulate cellular localization and biological activities of various proteins involved in DDR. Recently it has been suggested that PARP1 plays a key role in Tdp1-dependent repair of Top1-induced DNA damage. Tdp1 inhibitors together with PARP1 and/or Topoisomerase 1 inhibitors have been considered as targets in cancer therapy.

There are different model systems available for studying various stages of HPV life cycle. Most of the work has been done in human primary epithelial keratinocytes. However, using these cells is relatively time consuming and expensive, especially for high-throughput screening to identify novel HPV inhibitors. In this disclosure a U2OS-based model system with dual-luciferase system was used to measure cell growth/toxicity of the compounds and HPV genome replication suitable for high-throughput screening (PCT/EP2016/057898). This system allows studying all three replication stages of various HPVs. The gene expression of HPVs in U2OS cells is almost identical to the one in keratinocytes, making it suitable for identification of new anti-HPV drugs. Moreover, replication mechanism and replication intermediates of various HPV subtypes seem to be identical to the ones seen in different keratinocyte cell-lines.

Human Papillomaviruses are important pathogens responsible for great number of various cancer cases worldwide. Regardless of the two existing vaccines, there is a need for antivirals against HPV infection because vaccines are only preventive and other types of therapies have proven to be unsuccessful. So far there are no specific HPV inhibitors available. High-throughput screening (HTS) of available chemical libraries is widely used technique to identify new inhibitors against various pathogens. However, by now there has not been a suitable model system for HT-screening of HPV-inhibitors.

This disclosure provides solutions to the above described problems.

SUMMARY OF THE INVENTION

This disclosure provides identification of several new HPV replication inhibitors through high-throughput screening of NCI Diversity set IV and customized chemical libraries with IC50 ranging from 2.5-60 µM. These compounds are highly specific to High-risk HPVs. At least four of these compounds inhibit Tdp1-PARP1-Top1cc pathway by characterizing their synergistic effect with Topoisomerase I inhibitor Campthotecin. Tdp1 and PARP1 are identified as essential cellular proteins necessary for HPV replication, and by use of the novel inhibitors it is shown that they are valid drug targets for the development of further antivirals.

Recently we have developed an HTS compatible Dual-luciferase based system for measuring HPV genome replication (PCT/EP2016/057898). By use of this model system for screening NCI Diversity Set IV library which consists of different classes of biologically active compounds 5 compounds were identified that inhibited HPV18 initial amplification in low-micro molar range. None of the identified compounds inhibit E1 and E2 dependent URR replication. Besides initial amplification four out of five compounds successfully inhibited stable maintenance phase of the viral replication. In addition, three compounds inhibited vegetative amplification which takes place in highly differentiated upper epithelia. These inhibitors or their analogues are therefore capable of eliminating different stages of HPV infection.

Additional compounds are also suggested as potential inhibitors due to certain structural similarities with the identified five compounds.

It is an object of this invention to provide compounds effective in eliminating different stages of HPV infection.

It is an object of his invention to treat human papilloma virus affected cells or a subject (e.g., in vitro or in vivo).

It is an object of this invention to provide compounds for treating cervical cancer.

It is an object of this invention to provide a method to treat HPV infection by administering to the subject or contacting infected cells with a pharmaceutical composition comprising one or more compounds as identified and described in this disclosure.

In one object of this invention to provide a method of treating HPV affected cells comprising contacting the cells with a compound described herein or a mixture of the compounds.

In another object of this invention to provide a method of treating HPV affected cells in a subject, comprising administering to a subject one or more compounds or pharmaceutical compositions described herein.

It is an object of this invention to provide antiviral compound for inhibiting one or more replication stages of Human Papilloma Virus, wherein the compound is selected from the group consisting of:

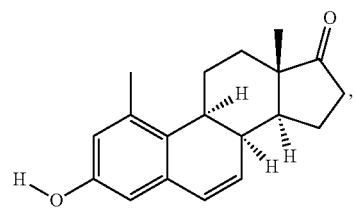

NSC 9782

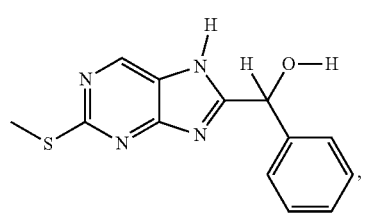

NSC 82269

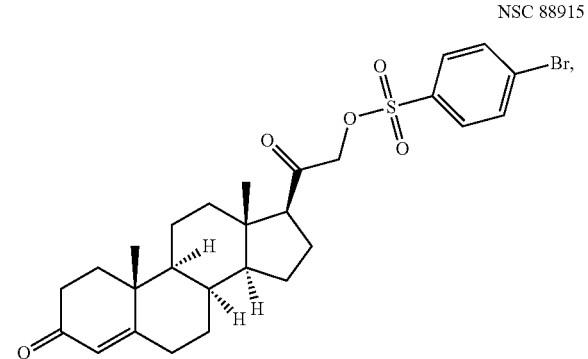

NSC 88915

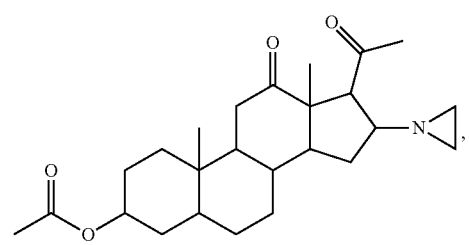

NSC 109128

-continued

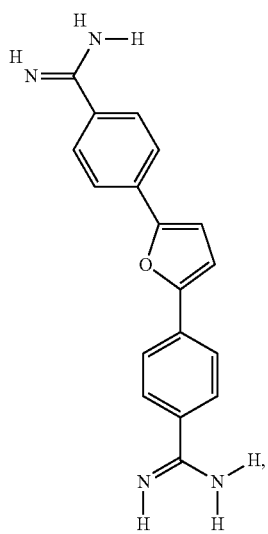
NSC 305831 and their analogs.

It is another object of this invention to provide an antiviral compound against high risk HPV, wherein the compound inhibits initial amplification, stable maintenance and vegetative replication phases of the high risk HPV and the compound is selected from the group consisting of: NSC109128, NSC305831 and NSC82269.

It is yet another object of this invention to provide an antiviral compound against high risk HPV, wherein the compound inhibits initial amplification and stable maintenance of high risk HPV, and the compound is NSC88915.

Yet another object of this invention is to provide an antiviral compound against high risk HPV, wherein the compound inhibits initial amplification phase of high risk HPV and the compound is NSC109128, NSC305831, NSC82269, NSC 88915 or NSC 9782.

It is an object of this invention to provide an antiviral compound against HPV 16HPV 18, HPV31, HPV33, HPV45.

Still another object of this invention is to provide an antiviral compound to inhibit one or more replication phases of Human Papilloma Virus, wherein the compound inhibits release of Topoisomerase I cleaving complex Top1cc from a high risk HPV DNA.

Another object of this invention is to provide an antiviral compound to inhibit one or more replication phases of HPV, wherein the compound inhibits the release by inhibiting Tpd1 or PARP1.

It is yet another object of this invention to provide a method to treat high risk HPV-infection, said method comprising administration of or contacting infected cells with a compound capable of inhibiting one or more replication phases of Human Papilloma Virus, wherein the compound inhibits release of Topoisomerase I cleaving complex Top1cc from HPV DNA.

Still further object of this invention is to provide a method to treat high risk HPV-infection, said method comprising administration of or contacting infected cells with a compound capable of inhibiting one or more replication phases of Human Papilloma Virus, wherein the compound inhibits Tpd1 or PARP 1.

Yet another object of the invention is to provide a method to treat high risk HPV infection said method comprising administration of or contacting infected cell with a compound selected from the group consisting of:

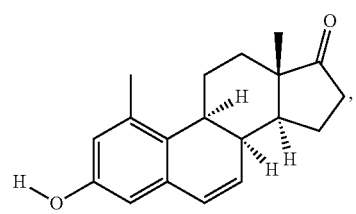
NSC 9782

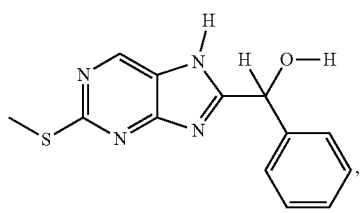
NSC 82269

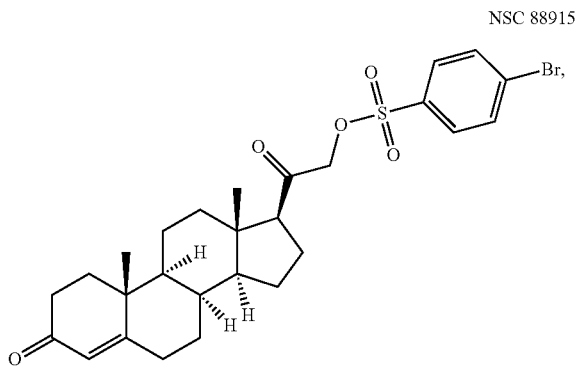
NSC 88915

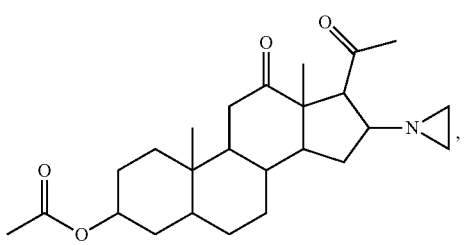
NSC 109128

NSC 305831

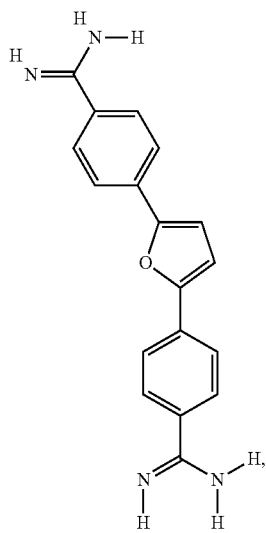

and their analogs.

It is a further object of this invention to provide a method to inhibit one or more replication phases of high risk HPV in vitro or in vivo, said method comprising a step of contacting the infected cell with a compound inhibiting release of Topoisomerase I cleaving complex Top1cc from HPV DNA.

It is still another object of this invention to provide a method to inhibit one or more replication phases of high risk HPV in vitro or in vivo, said method comprising a step of contacting the infected cell with a compound inhibiting Tpd1 or PARP 1.

Another object of this invention is to provide a method to inhibit one or more replication phases of high risk HPV in vitro or in vivo, said method comprising a step of contacting the infected cell with a compound selected from the group consisting of:

NSC 9782

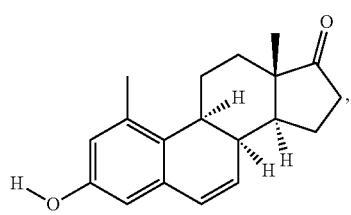

NSC 82269

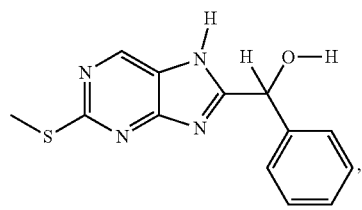

NSC 88915

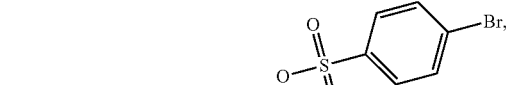

NSC 109128

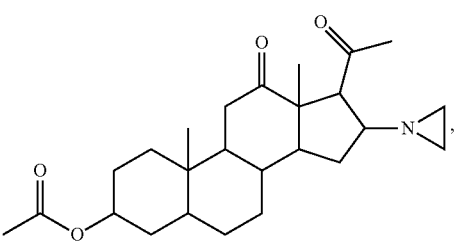

NSC 305831

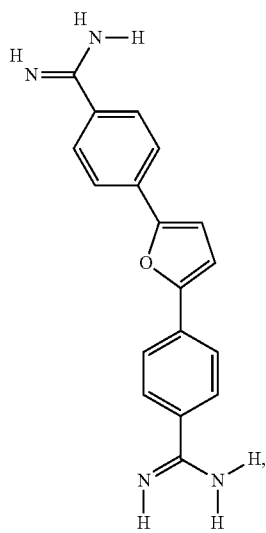

and their analogs.

A further object of this invention is to provide a medicament for treating high risk HPV infection, said medicament comprising one or more of compounds inhibiting release of Topoisomerase I cleaving complex Top1cc from HPV DNA.

Another object of the invention is to provide a medicament for treating high risk HPV infection, said medicament comprising one or more of compounds inhibiting Tpd1 or PARP.

Still another object of this invention is to provide a medicament for treating high risk HPV infection, said medicament comprising one or more of compounds selected from the group consisting of:

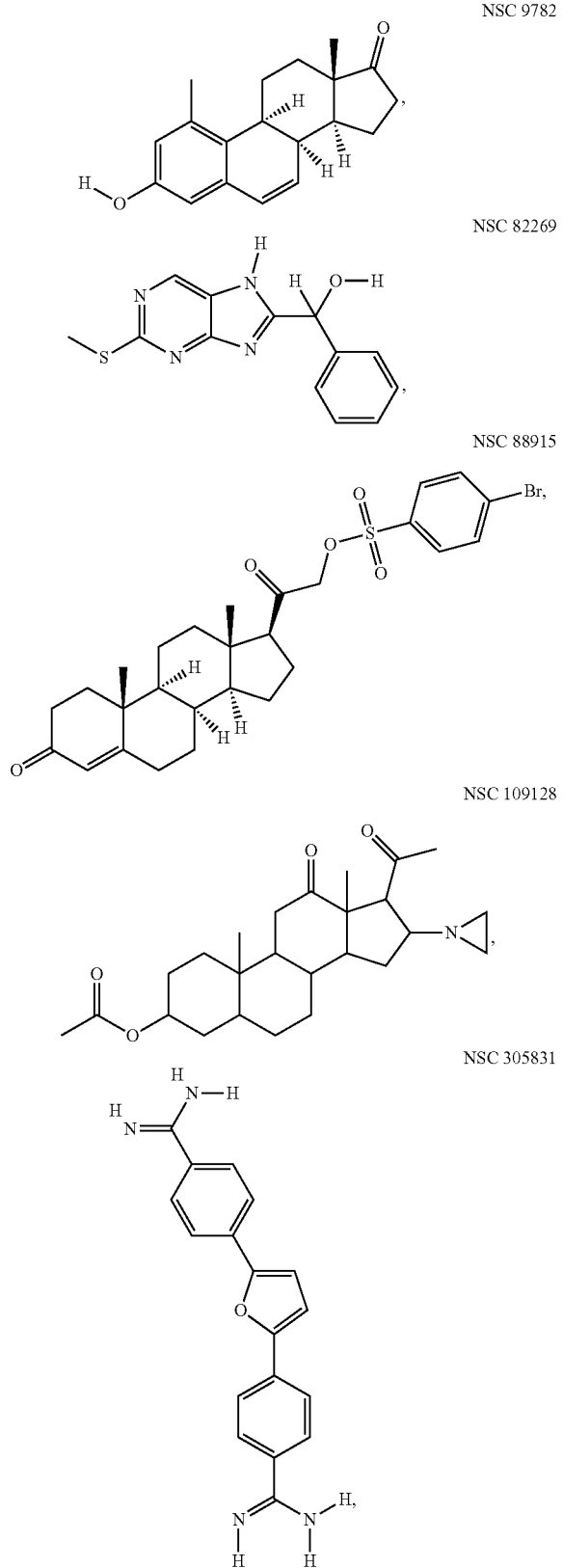

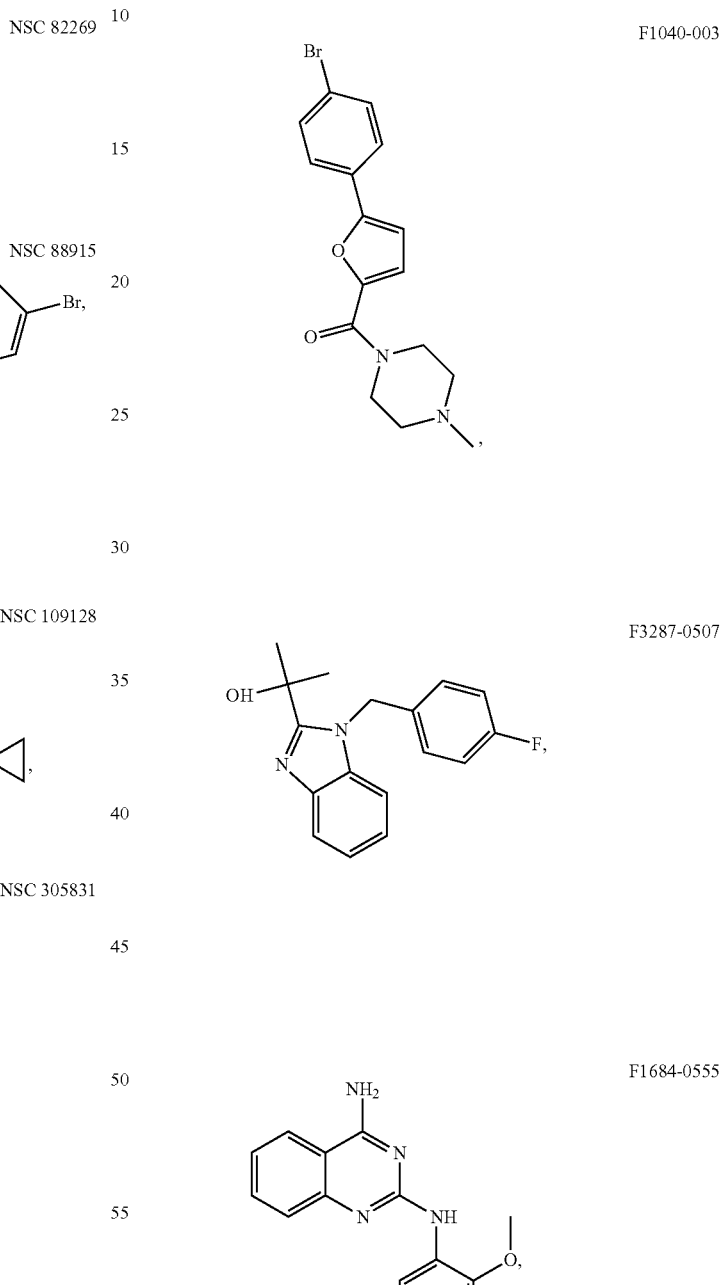

and their analogs.

Yet another object of this invention is to provide a method to identify potential antiviral compounds for inhibition of high risk HPV genome replication, said method comprising detection of compounds capable of inhibiting Tdp1 and PARP 1.

Still another object of this invention is to provide potential inhibitors of HPV infection or potential inhibitors of one or more HPV replication phases, said inhibitors being selected from the group consisting of:

and their analogs.

Another object of the invention is to provide medicament for treating HPV infections, said medicament comprising one or more of the compounds selected from the group consisting of:

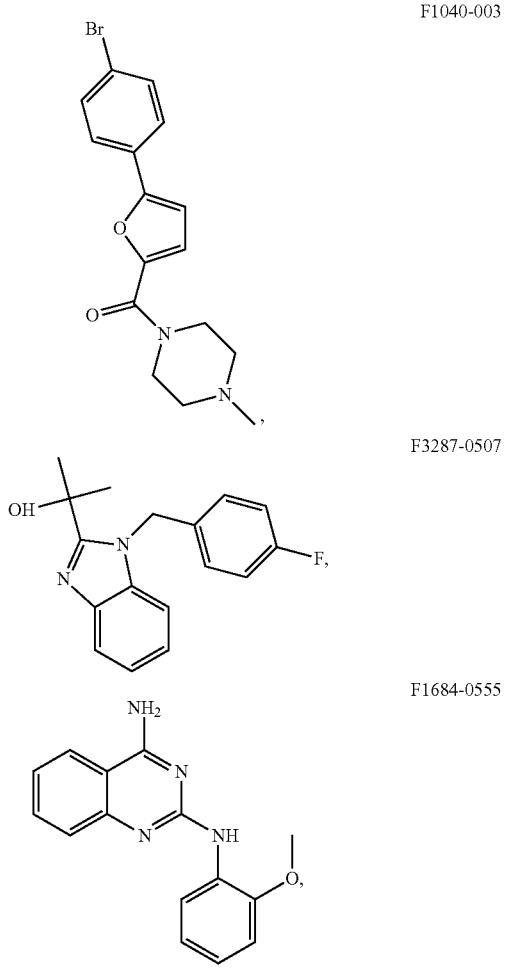

F1040-003

F3287-0507

F1684-0555 and their analogs.

DETAILED DESCRIPTION OF THE INVENTION

Definitions

Figure 1:
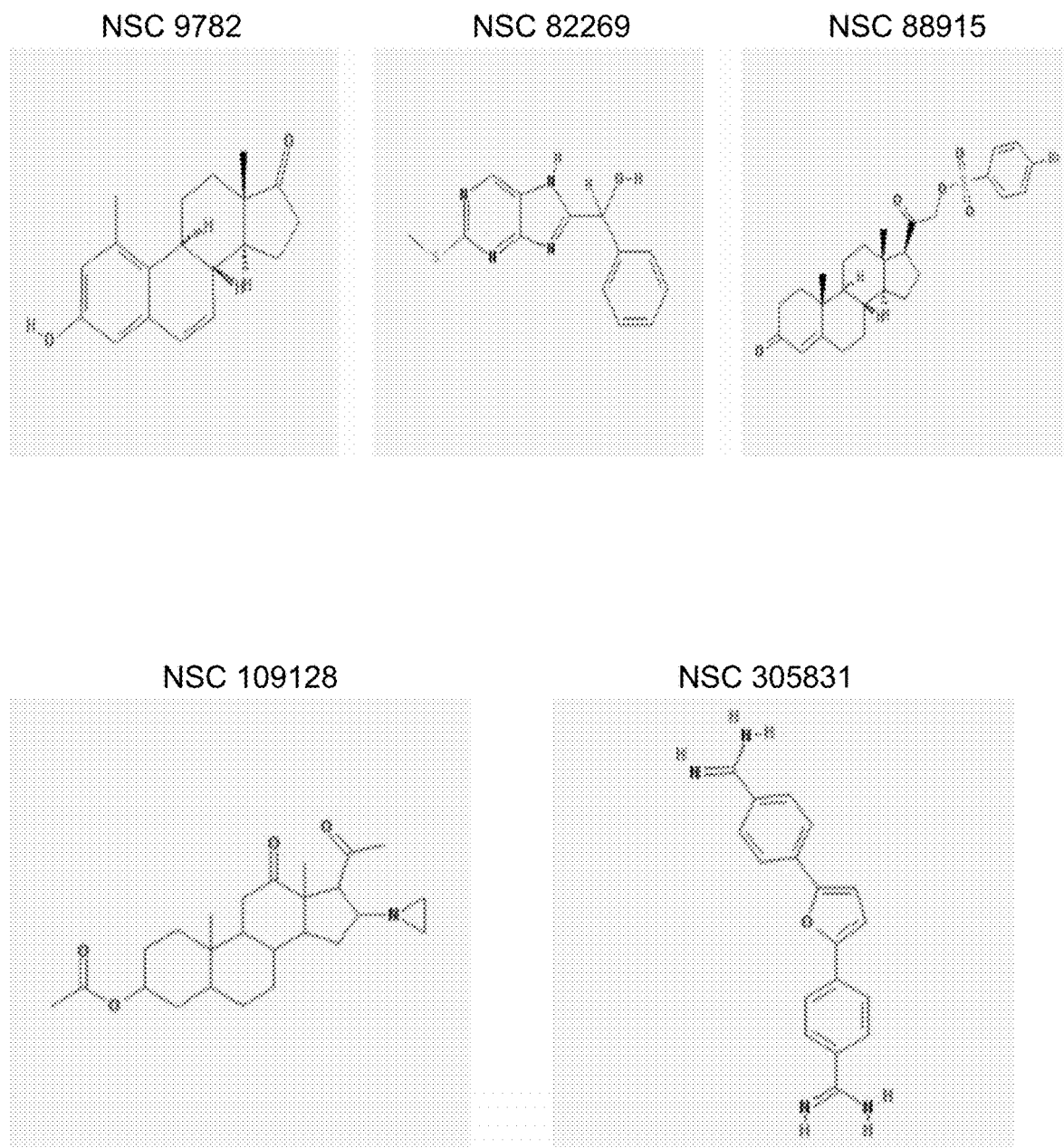
FIG. 1 Schematic 2D-structures of the five HR-HPV replication inhibitors identified during the HT-screen of NCI Diversity Set IV.

As used throughout this disclosure, the following terms, unless otherwise indicated, shall be understood to have the following meanings. If a definition is missing, the conventional definition as known to one skilled in the art controls. If a definition provided herein conflicts or is different from a definition provided in any cited publication, the definition provided herein controls.

As used herein, the terms "including", "containing", and "comprising" are used in their open, non-limiting sense.

As used herein, the singular forms "a", "an", and "the" include plural referents unless the context clearly dictates otherwise.

As used herein, the term "subject" encompasses mammals and non-mammals. Examples of mammals include, but are not limited to, any member of the Mammalian class: humans; non-human primates such as chimpanzees, and other apes and monkey species; farm animals such as cattle, horses, sheep, goats, swine; domestic animals such as rabbits, dogs, and cats; and laboratory animals including rodents, such as rats, mice and guinea pigs, and the like. Examples of non-mammals include, but are not limited to, birds, fish and the like. In one embodiment of the present invention, the mammal is a human.

The term "inhibitor" refers to a molecule such as a compound, a drug, an enzyme activator, or a hormone that blocks or otherwise interferes with a particular biologic activity.

The term "HPV replication inhibitor" means a compound capable of partially or fully to inhibit or block or interfere with one or more phases of HPV replication cycle.

The terms "effective amount" or "therapeutically effective amount" refer to a sufficient amount of the agent to provide the desired biological result. That result can be reduction and/or alleviation of the signs, symptoms, or causes of a disease or medical condition, or any other desired alteration of a biological system. For example, an "effective amount" for therapeutic use is the amount of a compound, or of a composition comprising the compound, that is required to provide a clinically relevant change in a disease state, symptom, or medical condition. An appropriate "effective" amount in any individual case may be determined by one of ordinary skill in the art using routine experimentation. Thus, the expression "effective amount" generally refers to the quantity for which the active substance has a therapeutically desired effect.

As used herein, the terms "treat" or "treatment" encompasses both "preventive" and "curative" treatment. "Preventive" treatment is meant to indicate a postponement of development of a disease, a symptom of a disease, or medical condition, suppressing symptoms that may appear, or reducing the risk of developing or recurrence of a disease or symptom. "Curative" treatment includes reducing the severity of or suppressing the worsening of an existing disease, symptom, or condition. Thus, treatment includes ameliorating or preventing the worsening of existing disease symptoms, preventing additional symptoms from occurring, ameliorating or preventing the underlying metabolic causes of symptoms, inhibiting the disorder or disease, e.g., arresting the development of the disorder or disease, relieving the disorder or disease, causing regression of the disorder or disease, relieving a condition caused by the disease or disorder, or stopping the symptoms of the disease or disorder.

This invention also relates to pharmaceutically acceptable prodrugs of the identified compounds, and treatment methods employing such pharmaceutically acceptable prodrugs. The term "prodrug" means a precursor of a designated compound that, following administration to a subject, yields the compound in vivo via a chemical or physiological process such as solvolysis or enzymatic cleavage, or under physiological conditions (e.g., a prodrug on being brought to physiological pH is converted to the compound). A "pharmaceutically acceptable prodrug" is a prodrug that is non-toxic, biologically tolerable, and otherwise suitable for formulation and/or administration to the subject. Illustrative procedures for the selection and preparation of suitable prodrug derivatives are described, for example, in "Design of Prodrugs", ed. H. Bundgaard, Elsevier, 1985. Examples of prodrugs include pharmaceutically acceptable esters of the compounds of the invention, which are also considered to be part of the invention.

Initial replication or amplification or transient replication or amplification refers to HPV DNA replication at establishment of the infection.

Stable maintenance or latent maintenance refers to the latent stage of viral replication cycle where viral DNA is stably maintained at an almost constant copy number in dividing host cells.

Vegetative amplificational replication or late amplificational replication refers to exponential viral DNA amplification in highly differentiated keratinocytes in the upper parts of the epithelium.

Figure 2:
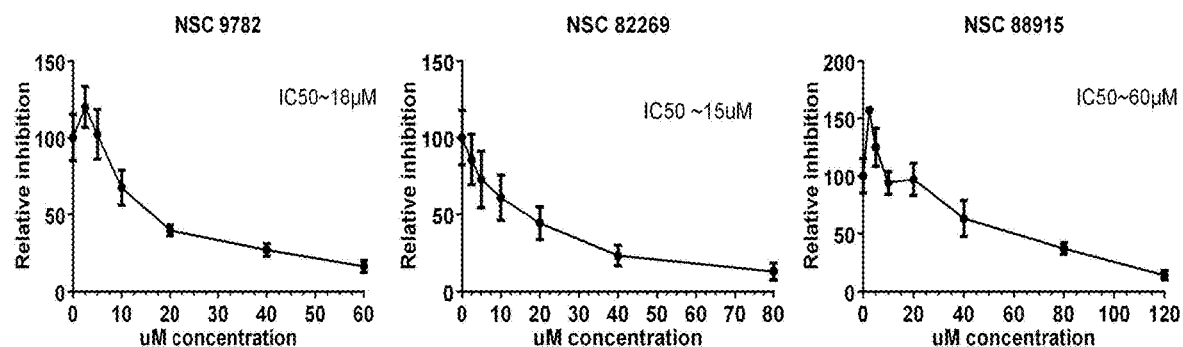
FIG. 2 Effect of the identified five compounds on HPV18 initial amplification. A: U2OS cells were transfected with HPV18 wt minicircle and grown in the presence of the compounds with indicated concentrations for 5 days. Genomic DNA was extracted, linearized, and digested with DpnI. HPV genome replication signals were detected using Southern Blot analyses and quantified with phosphoimager and expressed relative to vehicle control (DMSO). Approximate IC50 values are shown for each compound. Error-bars represent standard deviation from at least three independent experiment. B: U2OS cells were transfected with the expression vectors of HPV18 E1 and E2 proteins together with HPV18 URR (origin) minicircle plasmid. The cells were grown in the presence of the compounds with indicated concentrations for 24 or 48 hours. Genomic DNA was extracted, linearized and digested with DpnI. HPV URR replication signals were detected by Southern Blot analyses. DMSO serves as vehicle control and M 18URR serves as size marker.
Figure 2:
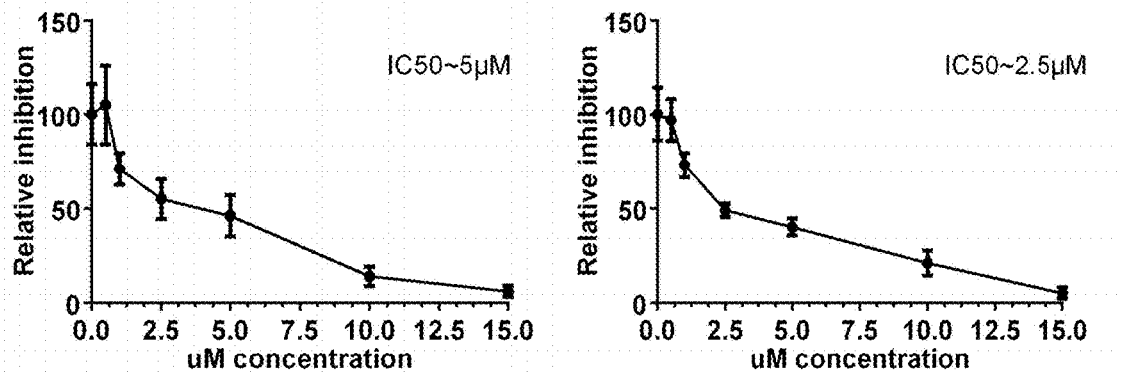
Figure 2:
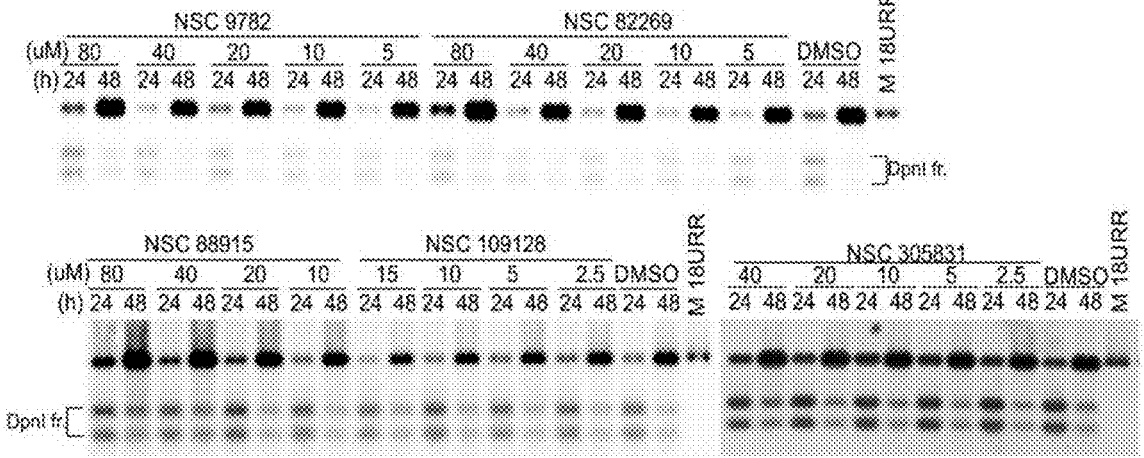
Figure 3:
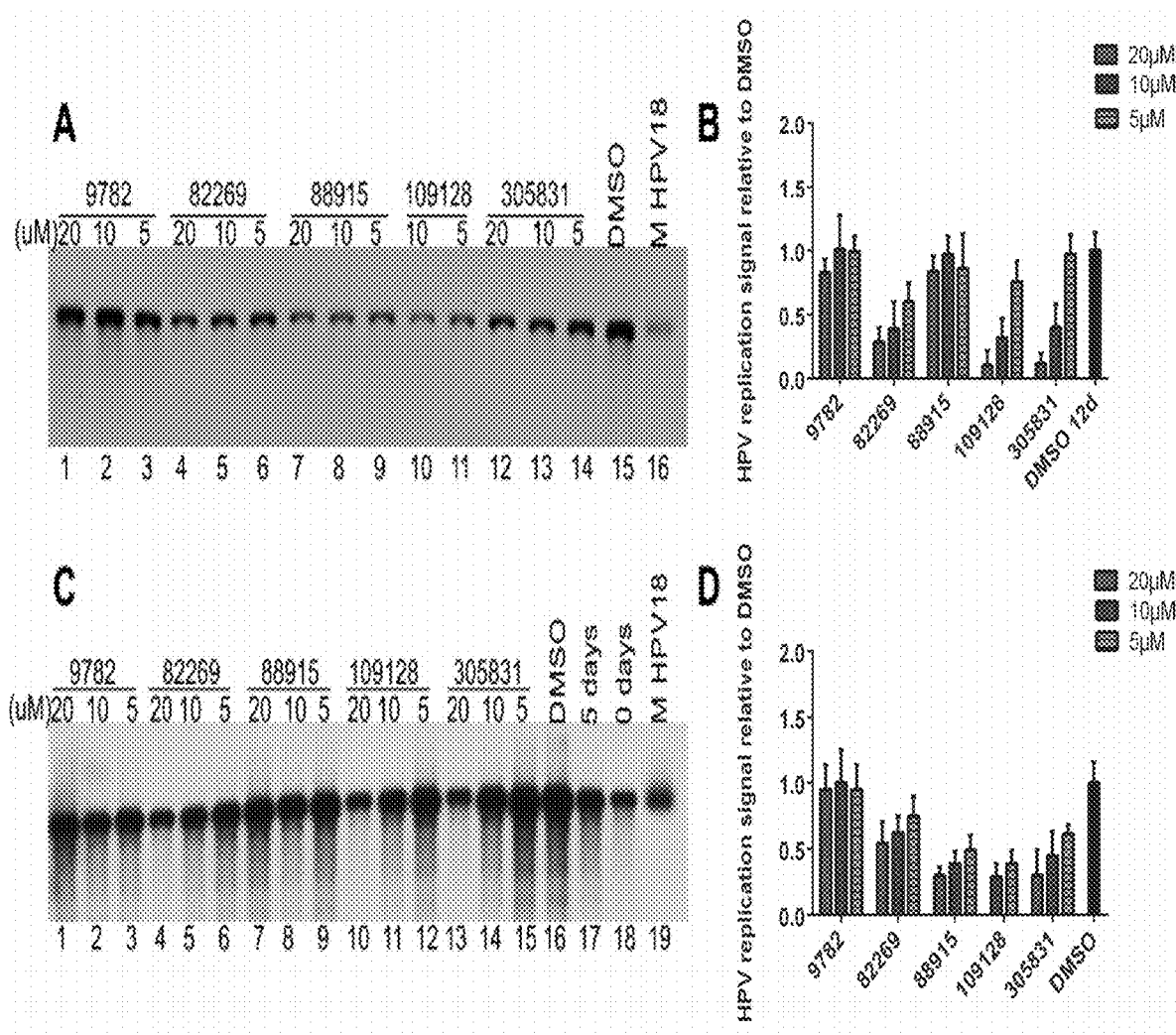
FIG. 3 Effect of compounds on stable maintenance and vegetative amplification of HPV18. A: U2OS #1.13 cells were grown in subconfluent conditions in the presence of the identified five compounds for 7 days. Genomic DNA was extracted, linearized and HPV replication signal was detected by Southern Blot and B: quantified by phosphoimager. C: U2OS #1.13 were seeded and grown for 5 days without splitting. On the $5^{th}$ day indicated concentrations of compounds were added to the media and the cells were grown for additional 7 days without splitting. On the $12^{th}$ day genomic DNA was extracted, linearized and HPV replication signal was detected by Southern Blot and D: quantified by phosphoimager. Error-bars represent standard deviations from at least two independent experiments.

Human Papillomaviruses are important pathogens responsible for great number of various cancer cases worldwide. Regardless of the two vaccines, there is still need for antivirals against HPV infection because vaccines are only preventive and other types of therapies have proven to be unsuccessful. So far there are no specific HPV inhibitors available. High-throughput screening (HTS) of available chemical libraries is widely used technique to identify new inhibitors against various pathogens. However, HTS requires suitable model systems which allow rapidly and accurately measure the effect of chemical compounds on target(s). Recently we have developed an HTS compatible Dual-luciferase based system for measuring HPV genome replication (PCT/EP2016/057898). Here we used this model system for screening NCI Diversity Set IV library which consists of different classes of compounds that have shown some kind of biological activity. We identified 5 compounds (FIG. 1) that inhibited HPV18 initial amplification in low-micromolar range (FIG. 2, panel A). Several studies regarding HPV replication have been carried out by measuring E1 and E2 dependent replication of HPV URR (contains the origin or replication) plasmid. Even HTS model system for measuring URR replication has been developed. The compounds identified here do not inhibit E1 and E2 dependent URR replication (FIG. 2, panel B), indicating that different cellular proteins could be used to facilitate HPV genome replication and/or that the replication mechanism of viral genome differs from the URR plasmid replication. Besides initial amplification four out of five compounds successfully inhibited stable maintenance phase of the viral replication (FIG. 3, panel A). In addition three compounds inhibited vegetative amplification which takes place in highly differentiated upper epithelia (FIG. 3, panel B). These inhibitors or their analogues are therefore capable of eliminating different stages of HPV infection.

Figure 4:
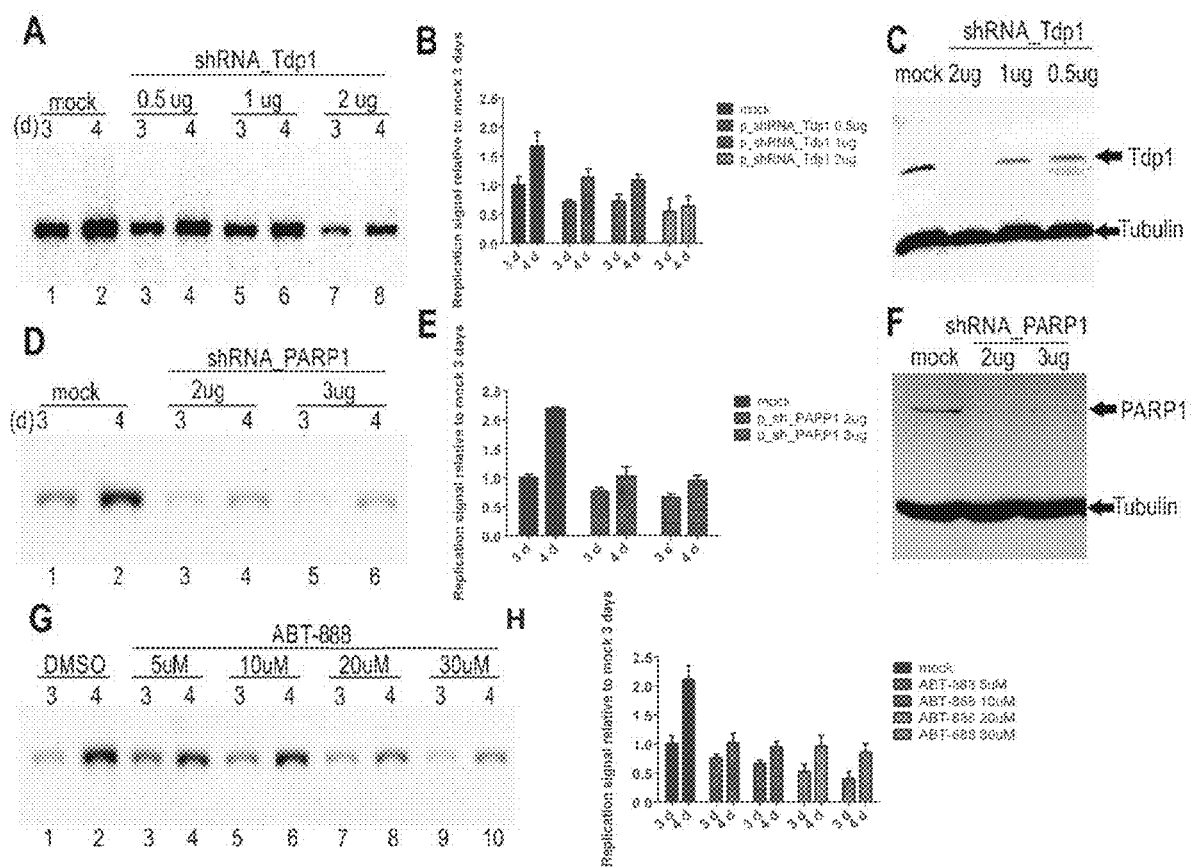
FIG. 4 Involvement of Tdp1 and PARP1 in HPV18 initial amplification. A: U2OS cells were transfected with HPV18 wt minicircle and sh_Tdp1 plasmid. Genomic DNA was extracted 3 and 4 days after the transfection, linearized and digested with DpnI. HPV replication signal was detected with Southern Blot analyses and B: quantified with phosphoimager. C: Western Blot analyses showing downregulation of Tdp1 protein by shRNA. D: U2OS cells were transfected with HPV18 wt minicircle and sh_PARP1 plasmid. HPV replication signal was detected with Southern Blot analyses and E: quantified with phosphoimager. F: Western Blot analyses showing downregulation of PARP1 protein by shRNA. G: U2OS cells were transfected with HPV18 wt minicircle and grown for 3 and 4 days in the presence of different concentrations of PARP1 inhibitor ABT-888. HPV replication signal was detected with Southern Blot analyses and H: quantified with phosphoimager. Error-bars represent standard deviations from at least three independent experiments.
Figure 5:
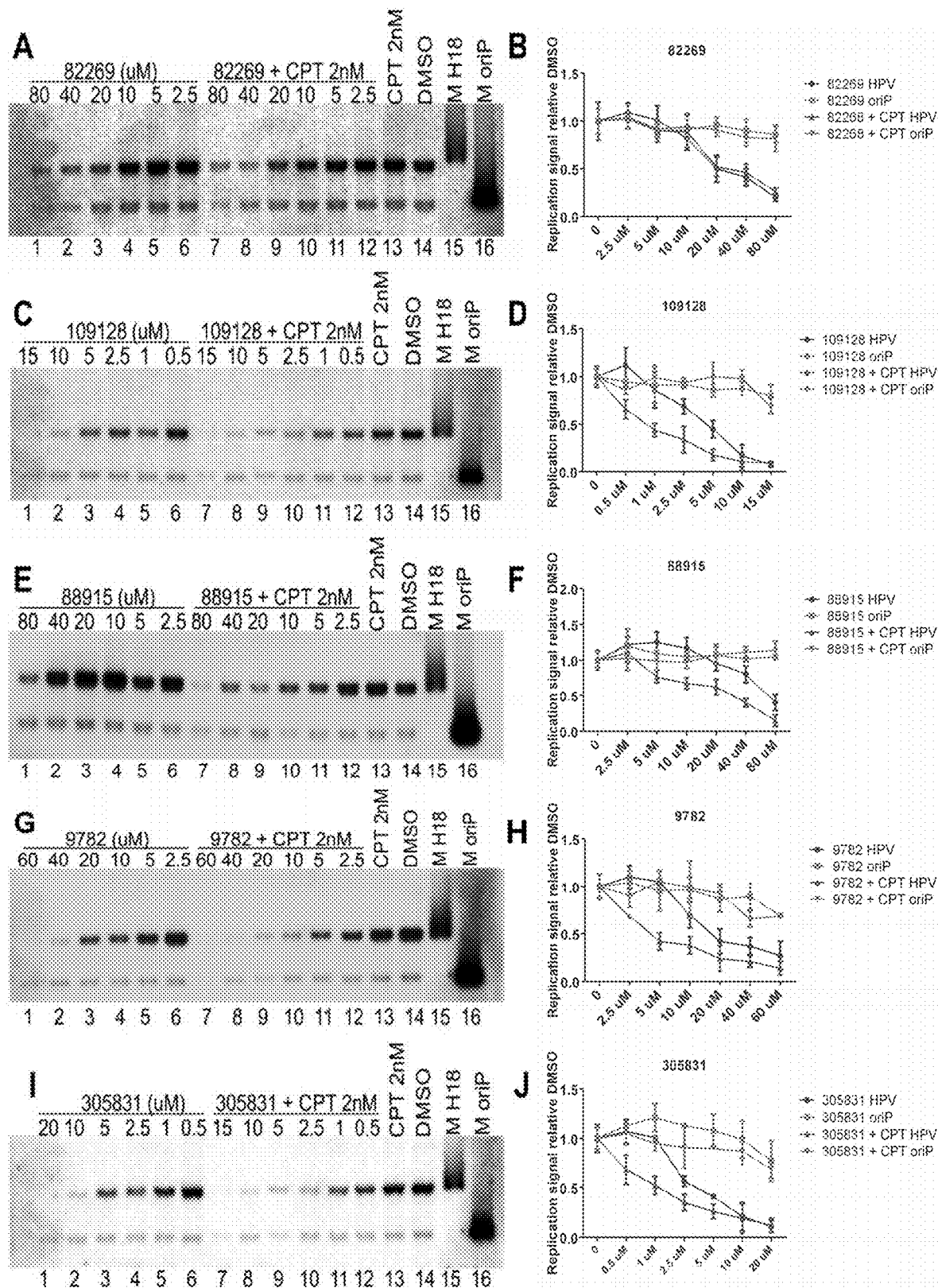
FIG. 5 Synergistic effect between Camptothecin (CPT) and the identified five compounds. U2OS-EBNA1 cells were transfected with HPV18 wt and oriP plasmids and grown in the presence of indicated concentrations of the compounds alone or together with 2 nM CPT for 5 days. Genomic DNA was extracted, linearized and digested with DpnI. Both HPV18 and oriP replication signals were detected with Southern Blot and quantified by phosphoimager. Compounds 109128, 88915, 9782 and 305831 show clear synergistic inhibition together with CPT (panels C-J), whereas compound 82269 does not (panels A and B). Error-bars represent standard deviations from at least three independent experiments.

It has become clear in the recent years that HPVs activate DNA damage response network during their replication to "invite" cellular replication and DNA repair proteins to its replication foci. Moreover, it has been shown that HPV uses Homologous recombination to efficiently replicate its genome. The exact mechanism and all the necessary cellular partners are however, not known yet. Tdp1 releases entrapped Top1cc from DNA and thereby preventing replication/transcription fork collision. Tdp1 is not absolutely necessary protein during normal replication as Top1 cleaving complexes get trapped due to certain types of DNA damage. Here we show that Tdp1 together with its regulator protein PARP1 are important cellular partners in HPV18 replication (FIG. 4) thus making those proteins good targets for developing HPV inhibitors. Camptothecin (CPT) is a Topoisomerase I inhibitor, it stabilizes Top1cc-DNA complex. In this disclosure it is shown that four of the five identified compounds show synergistic inhibition of HPV18 initial amplification with CPT suggesting that they inhibit Tdp1or have some other target related to releasing Top1cc complexes from DNA (FIG. 5). These results suggest that at some point during HPV replication Top1cc complexes get trapped on the viral genome. Tdp1 seems to be then activated probably by PARP1 and recruited on HPV DNA where it releases those complexes allowing replication to continue. When Tdp1 is inhibited, abnormal replication intermediates emerge, and HPV replication cannot be completed. None of the compounds inhibited HPV11 or HPV5 replication (FIG. 6), which indicates that Top1cc is not be entrapped on those HPV genomes and Tdp1 is therefore not necessary or not a limiting factor for low-risk or cutaneous HPV replication. It is possible that high-risk HPV E1 or some other proteins interacts with Tdp1 and brings it to the replication sites but low-risk or cutaneous HPV proteins do not.

During this work we used HPV HT-screening model system which we developed to screen for compounds capable of inhibiting HPV genome replication. We have identified five compounds: three of them inhibit all HPV replication stages, one of them inhibits initial amplification and stable maintenance and one only the initial amplification. In addition, we show here for the first time that during HPV18 replication, probably due to DNA damage, Topoisomerase I cleaving complexes get trapped on viral genome. To continue normal replication Tdp1 together with PARP1 are necessary for releasing Top1cc from HPV genome. Inhibition of the release of Top1cc from HPV DNA serves as promising target for antiviral development.

The present invention provides compounds for treating HPV infected cells. The invention further provides a method of treating HPV infected cells comprising contacting the cells with an effective amount of an antiviral compound of this invention. A subject infected with HPV may be treated by a method, which comprises administering to the subject an effective amount of one or more compounds of this invention. The compound may be administered in the form of a pharmaceutical composition comprising one or more of the compounds and a pharmaceutically acceptable carrier.

One aspect of the invention is pharmaceutically acceptable compositions comprising one or more antiviral compounds identified in this disclosure. The pharmaceutical compositions may include carriers, adjuvants or vehicle and alternatively one or more additional active agents.

The pharmaceutical compositions, according to the method of the present invention, may be administered by using any amount and any route of administration effective for treating or lessening the severity of an HPV infection or disease.

The exact amount required will vary from subject to subject, depending on the species, age, sex, weight, diet, medical condition and general condition of the subject, the severity of the infection, the particular agent, its mode of administration, and the like.

Administration of the compounds may be a single daily dose, multiple, spaced doses throughout the day, a single dose every other day, a single dose every several days or any other appropriate regimens. The dosage can be determined routinely by using standard methods known in the art.

The pharmaceutically acceptable compositions of this invention can be administered to humans and other animals orally, rectally, parenterally, intracisternally, intravaginally, intraperitoneally, topically (as by powders, ointments, or drops), buccally, as an oral or nasal spray, or the like, depending on the severity of the infection being treated.

Injectable preparations may be formulated according to the known art using suitable dispersing or wetting agents and suspending agents.

Compositions for rectal or vaginal administration can be suppositories which comprise one or more compounds identified in this disclosure with suitable non-irritating excipients or carriers.

Solid dosage forms for oral administration include capsules, tablets, pills, powders, and granules. In such solid dosage forms, the active compound is mixed with at least one inert, pharmaceutically acceptable excipient or carrier. In the case of capsules, tablets and pills, the dosage form may also comprise buffering agents.

Oral formulations may also be syrups and elixirs.

Dosage forms for topical or transdermal administration of a compound of this invention include ointments, pastes, creams, lotions, gels, powders, solutions, sprays, inhalants or patches. The active component is mixed under sterile conditions with a pharmaceutically acceptable carrier and any needed preservatives or buffers as may be required. Additionally, the present invention contemplates the use of transdermal patches, which have the added advantage of providing controlled delivery of a compound to the body. Such dosage forms are prepared by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

More than one compound of the invention may be administered separately, simultaneously, or sequentially to infected cells, to tissue containing the infected cells, or to infected subjects.

It will also be appreciated that the compounds and pharmaceutically acceptable compositions of the present invention can be employed in combination therapies, that is, the compounds and pharmaceutically acceptable compositions can be administered concurrently with, prior to, or subsequent to, one or more other desired therapeutics or medical procedures.

The invention is now described by means of non-limiting examples.

Methods Used in the Experiments

Cell lines and transfection. U2OS (ATCC no: HTB-96), U2OS-EBNA1 (Icosagen Cell Factory OÜ), U20S-GFP-Fluc #10.15 (DMSZ deposit number ACC3258) were grown in Iscove's modified Dulbecco's medium (IMDM) supplemented with 10% fetal calf serum (FCS). All U2OS cell-lines were transfected by electroporation (220V; 975 µF) with a Bio-Rad Gene Pulser X-cell supplied with a capacitance extender (Bio-Rad Laboratories).

Plasmids. The parental plasmids pMC-HPV18 for HPV18 wt minicircle production was constructed by adding BglII restriction site (used for cloning into pMC.BESBX vector [54]) into HPV18 genome between nt. 7473 and nt. 7474 (herein, the numbering of the HPV18 genome is according to the NCBI Reference Sequence NC_001357.1) which have been shown no alterations in the gene expression and replication. The parental plasmid pMC-HPV18-RlucE2

(DMSZ deposit number DSM 29865) was constructed based on pMC-HPV18. The parental plasmid pMC-HPV5 was constructed by using XmaJI restriction site in the ORF of L2 protein. The parental plasmid pMC-HPV11 was constructed by using BamHI restriction site in the HPV11 genome. The parental plasmid pMC-HPV33 was constructed by using Eco81I restriction site in the HPV33 genome. The parental plasmid pMC-HPV45 was constructed by using AscI restriction site in the HPV45 genome. The HPV31 genome sequence cloned in pBR322 vector was obtained from the International Human Papillomavirus (HPV) Reference Center. The parental plasmid pMC-HPV18URR contains 206 nucleotides from the end of L1 ORF, full-length HPV18 URR and 14 nucleotides from the beginning of E6 ORF. This fragment was cloned into the BglI site in pMC.BESBX vector. The pMC.BESBX vector contains bacterial origin of replication and kanamycin resistance gene necessary for propagation in bacterial cells and additional elements for minicircle production. Minicircle HPV genomes were produced in E. coli strain ZYCY10P3S2T as described in [54]. The pMC-HPV containing E. Coli strain ZYCY10P3S2T was grown in Terrific Broth media (Life Technologies) at 37° C. for 16-18 h, after which equal amount of LB media containing 0.02% L-arabinose and 20 mM NaOH was added and culture was grown at 32° C. for 8 hours to induce recombination and production of supercoiled minicircles. Finally, the HPV genomes were purified from E. coli with the QIAfilter Plasmid kit (Qiagen). The resulting minicircle HPV genomes have less than 100 bp of non-HPV sequence. For generation of HPV31 genome for transfection, HPV31 plasmid was digested with EcoRI, resolved in agarose gel, HPV31 sequence was purified from gel and religated. Expression vectors for HPV18 E1 and E2 are described in [36]. Ebstein Barr Virus oriP plasmid p994 was a kind gift from B. Sugden, described in [55]. ShRNA expression was under the control of RNA polymerase III promoter U6.

```
Tdp1 shRNA sequence:
                                            (SEQ ID NO: 1)
GCACGATCTCTCTGAAACAAACTCGAGTTTGTTTCAGAGAGATCGT PARP1 shRNA sequence:
                                            (SEQ ID NO: 2)
GGACTCGCTCCGGATGGCCTTCAAGAGAGGCCATCCGGAGCGAGTCC
```

High-throughput screen for identification of HPV18 inhibitors. The U2OS-GFP-Fluc #10.15 were transfected with 2 ug of HPV18-Rluc-E2 minicircle and the cells were seeded onto 100 mm plates. On the next day, the cells were detached and seeded onto 96-well plates (5000 cells per well). 48 hours after the transfection screened compounds were added to the media in 5 uM and 1 uM concentrations. The cells were grown for three days and both Firefly luciferase (shows cellular viability) and Renilla luciferase (shows HPV copy number) were measured using Dual-Glo luciferase assay system (Promega) according to manufacturer's protocol with the GloMAX-96 luminometer (Promega). The results were blotted on a XY-scatter diagram and HPV-specific hits were chosen.

Chemicals. The Diversity set IV and additionally compounds NSC9782, NSC 88915, NSC 82269, NSC 109128 and NSC305831 were obtained from Drug Synthesis and Chemistry Branch, Developmental Therapeutics Program, Division of Cancer Treatment and Diagnosis, National Cancer Institute USA. Camptothecin (CPT) (sc-200871) and ABT-888 (sc-202901) were purchased from Santa Cruz Biotechnology.

Replication assay. The U2OS or U2OS-EBNA1 cells were transfected with 2 ug of HPV18 minicircle genome and 1ug of oriP plasmid (only in case of U2OS-EBNA1 cells). All the compounds were added to the media immediately after the transfection and media was changed on the third day. Replication signals were detected with Southern Blot method. Briefly, genomic DNA was extracted 3 and 4 days after the transfection with sh_RNAs or with the use of ABT-888 and 5 days after for analyses of the effects of HPV inhibitors w/wo CPT. DNA was digested with BglI and DpnI for analyses of HPV18 replication and with BstXI, ScaI and DpnI for analyses of HPV18 and oriP replication simultaneously. 3 ug of DNA was resolved in agarose gel, transferred to a nylon membrane (Membrane Solutions LLC) and hybridized with specific radioactively labeled probes. Signals were detected and quantified with Typhoon Trio+ phosphoimager (GE Healthcare) and exposed on an X-ray film (AGFA).

HPV copy number quantitation. Quantitative real-time PCR (qPCR) was used to evaluate the effect the compounds had on HPV11 and HPV5 replication. U2OS cells were transfected with 2 μg of the HPV11 or HPV5 minicircle, compounds were added to the media immediately after the transfection and again on the $3^{rd}$ day when the media was changed. Genomic DNA was extracted 5 days after the transfection, the samples were linearized with HindIII (for HPV11) and SacI (for HPV5) and digested with DpnI to fragment input DNA. For each qPCR reaction, 3 ng of DNA was used. The reactions were performed with EvaGreen qPCR Mix Rox (Solis BioDyne) according to the manufacturer's protocol using 7900 HT Fast Real-Time PCR System (Applied Biosystems). Oligonucleotides (300 nM of each per reaction):

```
HPV11:
                                            (SEQ ID NO: 3)
    5'-AGCATGCAGACACATCAGGAATATTAG-3'
    and (SEQ ID NO: 4)
    5'-GTGCCGATTGGGTGGTTGCAGGATTTG-3';

HPV5:
                                            (SEQ ID NO: 5)
    5'-GGTTGCAGGAACTGTGAGGT-3'
    and (SEQ ID NO: 6)
    5'-TCCGCGACAGTCGGGGCACAGG-3'.
```

The $Ct_{rDNA}$ was detected as a normalization standard from the ribosomal DNA gene sequence in the U2OS genome with the following oligonucleotides (300 nM of each):

```
                                            (SEQ ID NO: 7)
    5'-GCGGCGTTATTCCCATGACC-3'
    and (SEQ ID NO: 8)
    5'-GGTGCCCTTCCGTCAATTCC-3'.
```

The relative value $C_N$, which reflects the average viral genome copy number per cell, was calculated from the data with $\Delta Ct = Ct_{HPV} - Ct_{rDNA}$ and $C_N = 2^{-\Delta Ct}$.

Western Blot. The cells were lysed with Laemmli buffer (4% SDS, 20% glycerol, 120 mM Tris-Cl (pH 6.8), and 200 mM DTT) and boiled for 10 minutes at 100° C. Samples were resolved in SDS-PAGE gel and transferred to PVDF membrane Immobilon-P (Millipore). Tdp1 and PARP1 were detected with their specific antibodies from Santa Cruz Biotechnology: sc-365674 and sc-56197 respectively. Tubulin (used as loading control) was detected using Sigma Aldrich antibody T9026. Anti-mouse peroxidase conjugated secondary antibody (LabAS) and Amersham ECL Western Blotting Detection Kit (GE Healthcare) were used for visualization. Signals were exposed on an X-Ray film (AGFA).

Five Novel HPV Inhibitors Identified in High-Throughput Screening of NCI Diversity Set IV.

NCI Diversity set IV was screened as described in Example 1 with the previously characterized HPV model system (U.S. provisional application 62/145,243 Tdp1 shRNA sequence: GCACGATCTCTCT-GAAACAAACTCGAGTTTGTTTCAGAGAGATCGT (SEQ ID NO:1)

```
PARP1 shRNA sequence:
                                              (SEQ ID NO: 2)
GGACTCGCTCCGGATGGCCTTCAAGAGAGGCCATCCGGAGCGAGTCC
``` for compounds inhibiting initial amplification of HPV18 genome in U2OS cells. HT-screening was conducted with all the compounds in this library in 5 uM and 1 uM concentrations and it gave us 80 hits (approximately 5% of analyzed compounds). After validation of the hits on HPV18 wt genome, we found five compounds inhibiting initial amplification of HPV18 in U2OS cells (FIG. 1). To further characterize the compounds, we performed replication assay described in Example 1. Relative inhibition to vehicle control DMSO is shown on FIG. 2, panel A. All five compounds: NSC 9782, NSC82269, NSC 88915, NSC 109128 and NSC 305831, show concentration-dependent inhibition of HPV18 initial amplification, IC50 ranging from 2.5 to 60 uM.

We were curious if these identified compounds could inhibit E1 and E2 dependent replication of the plasmid containing HPV origin of replication—URR. We transfected U2OS cells with 25 ng of E1 and E2 expression vectors together with 500 ng of HPV18 URR minicircle plasmid and added various concentrations of compounds as indicated on FIG. 2, panel B. We detected HPV18 URR replication by Southern blot analyses and none of the compounds inhibited URR replication compared to the vehicle control DMSO (FIG. 2, panel B) indicating that different cellular proteins are used to facilitate HPV genome replication and/or replication machinery of viral genome differs from the URR plasmid replication. Another possibility is the difference in the levels of E1 and E2 proteins: the expression level during HPV genome replication is considerably lower than the level in URR replication assay.

Effect of compounds on stable maintenance and vegetative amplification.

Our U2OScell-based system is suitable for studying all three replication stages of various HPV subtypes. Stable maintenance phase could be monitored by maintaining HPV-positive cells in subconfluent conditions. We used HPV18 positive monoclonal U2OS cell-line #1.13 with viral copy number ~2000. We grew the #1.13 cells in the presence of various concentration of compounds in subconfluent conditions (cells were split every three days) for 7 days. HPV18 replication signal was detected by Southern blot analyses and quantified with phosphoimager. About 50% of the signal was lost in case of compound 82269 compared to the DMSO control (FIG. 3, panel A, compare lanes 4-6 with lane 15 and panel B). Compounds 88915, 109128 and 305831 showed even higher inhibitory effect—about 70% of the signal was lost during the 7-day period (FIG. 3, panel A, compare lanes 7-14 with lane 15 and panel B). In case of compound 9782, no significant reduction in signal could be detected (FIG. 3, panel A, lanes 1-3 and panel B). Thus four of the five identified compounds effectively blocked the stable maintenance of a high risk type HPV.

If #1.13 is grown in confluent conditions for at least 5 days, vegetative amplification of HPV genome is turned on. We seeded equal amounts of cells onto plates and grew them for 5 days without splitting. On the 5$^{th}$ day various concentrations of compound were added and the cells were grown for additional 7 days (media was changed every two days throughout the experiment). HPV replication signal was detected by Southern Blot analyses and quantified with phosphoimager. As can be seen on FIG. 3, panel C lanes 16-18, about 5-7-fold increase in the viral copy number occurs reminiscent of vegetative amplification. Compounds 109128 and 305831 almost completely abolished amplification in higher concentrations (FIG. 3, panel C, lanes 10-15, panel D). Compound 82269 also showed clear concentration-dependent inhibition of vegetative amplification (FIG. 3, panel C, lanes 4-6 and panel B). However, compounds 9782 and 88915 did not have any effect (FIG. 3, panel C, lanes 1-3 and 7-9, panel D).

In conclusion, compounds 109128, 305831 and 82269 clearly inhibit both stable maintenance and vegetative amplification of HPV18, 88915 only inhibits stable maintenance phase and 9782 does not inhibit any of the later replication stages.

Tdp1 and PARP1 are Involved in HPV18 Initial Amplification.

Two of the identified compounds, 88915 and 305831 are known to inhibit Tdp. To examine if Tdp1 is necessary for HPV18 initial amplification, we transfected U2OS cells with HPV18 genome together with various concentrations of shRNA_Tdp1 plasmid. Empty shRNA plasmid was used as mock control. Firstly, Tdp1 expression was evaluated and FIG. 4, panel C shows clearly that Tdp1 expression is decreased significantly through the use of shRNA_Tdp1. Next genomic DNA was extracted 3 and 4 days after the transfection and replication assay was performed. FIG. 4, panels A (compare lanes 1 and 2 with 3-8) and B show clear decrease in HPV18 replication when Tdp1 expression is downregulated.

It was recently shown that PARP1 is activating Tdp1 and recruiting it to sites of DNA damage. To examine if PARP1 is also involved in HPV18 replication, we transfected U2OS with HPV18 genome together with shRNA_PARP1 plasmid or empty shRNA vector. FIG. 4, panel F show that PARP1 expression is decreased due to shRNA_PARP1 expression. Genomic DNA was next extracted 3 and 4 days after the transfection and replication assay was performed to evaluate HPV18 initial amplification. FIG. 4, panels D (compare lanes 1 and 2 with 3-6) and E indeed show that downregulation of PARP1 inhibits HPV18 replication significantly.

PARP1 involvement in HPV18 replication was also evaluated using known PARP1 inhibitor ABT-888 (veliparib). U2OS cells were transfected with HPV18 genome and grown in the presence of various concentrations of ABT-888 for 3 and 4 days, DMSO serves as vehicle control. Replication assay was performed and FIG. 4, panels G (compare lanes 1 and 2 with 3-10) and H show that HPV18 replication is decreased through the use of PARP1 inhibitor ABT-888.

In conclusion the results demonstrate that both Tdp1 and PARP1 are important cellular partners in HPV18 replication.

Synergistic effect of Campthotecin (CPT) and HPV18 replication inhibitors. CPT is a Topoisomerase I inhibitor that stabilizes entrapped Top1cc complexes to DNA. Since Tdp1 is responsible for cleaving entrapped Top1cc complexes from DNA, synergistic effect between CPT and Tdp1 inhibitors occurs. In the experiments shown in FIG. 5 we used U2OS cells constitutively expressing Epstein Barr virus (EBV) EBNA1 protein—U2OS-EBNA1. These cells allow to monitor HPV and EBNA1 supported oriP plasmid replication simultaneously. During HPV initial amplification, viral genome is replicated several times during cell cycle, however EBNA1-dependent replication occurs once per cell cycle due to cellular control mechanisms, which suggest HPV and EBV use completely different replication mechanisms. U2OS-EBNA1 cells were cotransfected with HPV18 genome and oriP plasmid and the cells were grown in the presence of various concentrations of the identified HPV inhibitors alone or together with 2 nM of CPT for 5 days, DMSO was used as vehicle control. Replication assay was performed, signals were quantified with phosphoimager and results in FIG. 5 show that all of the HPV inhibitors are highly specific because none of them inhibited EBNA1 dependent replication of oriP plasmid. 2 nM CPT alone did not inhibit HPV18 initial amplification. In case of compounds 109128 (FIG. 5, panels C and D), 88915 (panels E and F), 9782 (panels G and H) and 305831 (panels I and J), clear concentration dependent synergistic effect together with CPT occurs as HPV replication is more efficiently inhibited (compare lanes 1-7 with 8-12 in all experiments). Compound 82269 (FIG. 5, panels A, compare lanes 1-7 with 8-12 and B) however, showed no synergistic effect together with CPT.

Compounds are not Universal HPV Inhibitors

Figure 6:
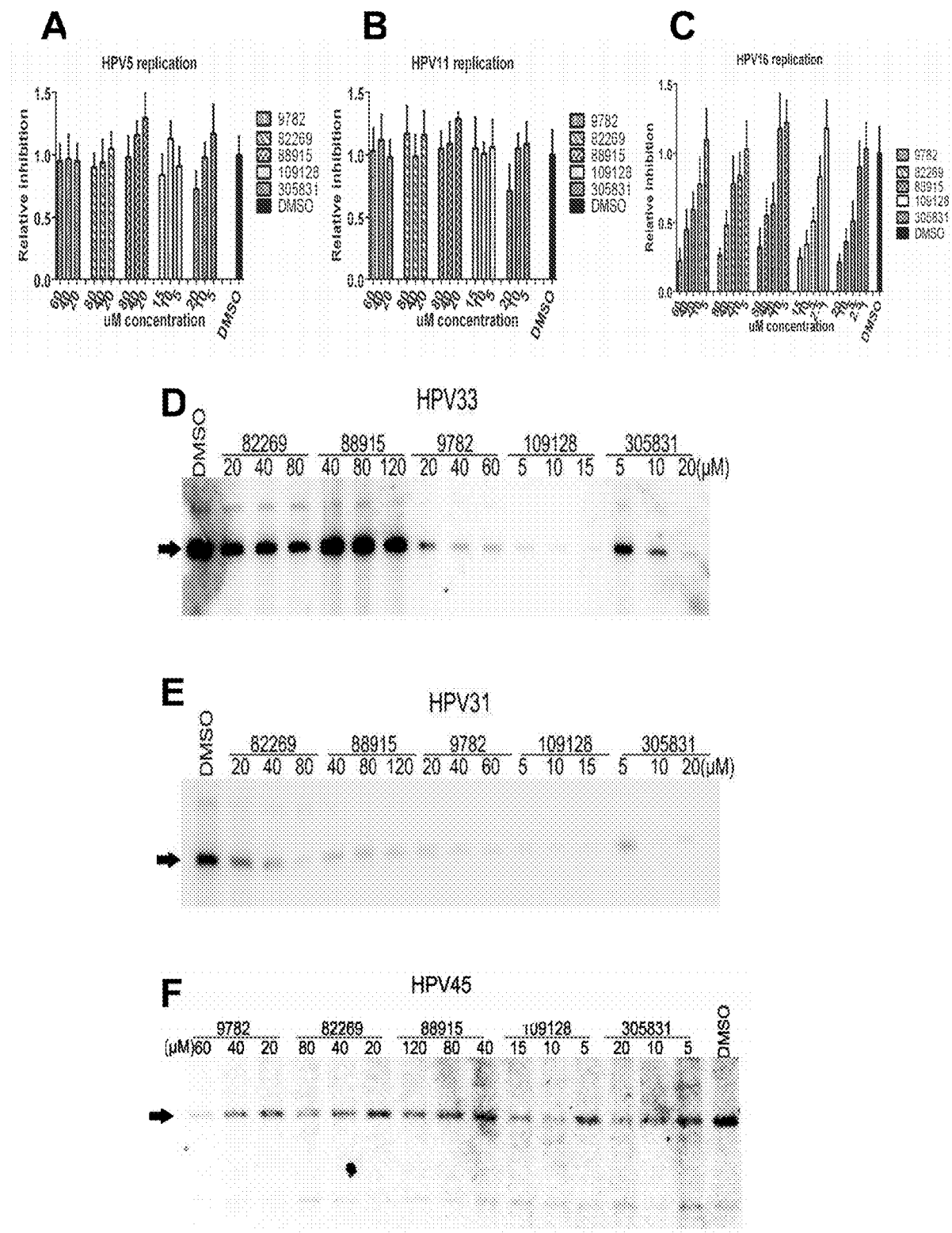
FIG. 6 Effect of the identified five compounds on different types of HPVs. U2OS cells were transfected with 3 μg of HPV 5, 2 μg of HPV11 and 5 μg of HPV16 minicircles and grown in the presence of indicated concentrations of compounds for 5 days. Genomic DNA was extracted, linearized and digested with DpnI. HPV replication signal was quantified using qPCR. A: Effect on HPV5. B: Effect on HPV11. C: Effect on HPV16 Error-bars represent standard deviations from two independent experiments. D, E and F: U2OS cells were transfected with 2 μg HPV33 minicircle, 5 μg of HPV45 minicircle and 2 μg of religated HPV31 genome and grown in the presence of indicated concentrations of compounds for 5 days. Episomal DNA was extracted using HIRT DNA extraction method, linearized and digested with DpnI. HPV replication signal detected by Southern Blot analyses. Black arrow indicates the replicated HPV signal.

To examine if the compounds identified here inhibit other HPV subtypes as well, U2OS cells were transfected with LR-HPV type 11 and cutaneous HPV type 5 genomes and grown in the presence of various concentrations of compounds for 5 days, media was changed on the 3$^{rd}$ day. DMSO was added as vehicle control. Genomic DNA was extracted, HPV DNA was linearized and digested with DpnI. HPV replication signals were quantified with qPCR analyses as described in the materials and methods section. Result on FIG. 6 show that none of the compounds inhibit HPV5 (FIG. 6, panel A) or HPV 11 (FIG. 6, panel B) initial amplification. However, compounds are active against HPV16 (FIG. 6, panel C), HPV33 (FIG. 6, panel D) and HPV31 FIG. 6, panel E). Accordingly, it seems that the compounds inhibit high risk HPV replication, including HPV 16, HPV 18, HPV31 and HPV33, but not the low risk and cutaneous HPV types.

Compounds Inhibit the Replication of HR-HPVs through the HPV Replication Proteins E1 or E2.

Besides oncoproteins E6 and E7, HPVs differ from replication proteins E1 and E2 as well. To determine if the compounds identified here inhibit the replication of HR but not LR or cutaneous HPVs through E1 or E2, HPV18E1E2 mutant genome (deficient in replication due to mutations in the ORFs of E1 and E2) was replicated by E1 and E2 proteins originating from HPV11. HPV18E1E2 mutant genome alone was used as control. U2OS cells were co-transfected with HPV18E1E2 mutant and HPV11 wt mini circle genome and the cells were grown in the presence of compound 305831 for 5 days, media was changed on the 3$^{rd}$ day. DMSO was added as vehicle control. Genomic DNA was extracted, HPV DNA was digested with AgeI, SdaI and DpnI. HPV replication was detected by Southern Blot analyses. Results on FIG. 7 show, that HPV18E1E2 mutant genome is indeed replication-deficient when transfected alone (lane 7). DMSO control on FIG. 7, lane 6 shows that HPV11 wt genome successfully complements the E1/E2 deficient HPV18 genome. In case of samples treated with the compound 305831, there is no inhibition of HPV18 replication which is carried out by the E1 and E2 proteins originating from HPV11 genome (FIG. 7, compare lanes 1-6 with 7). This data suggests that the compounds target either HR-HPV E1 or E2 protein or their interaction with cellular proteins. The activity of LR-HPV E1 and E2 proteins or their interactome seem to be different compared to HR-HPV replication proteins.

Further Potential Compounds for Inhibiting HPV Replication

Based on the structure of the identified five compounds that are effective in the inhibiting one or more phases of the HPV replication, we have identified the following three structures having certain similarities with the identified five compounds for potential compounds for use in inhibiting HPV replication.

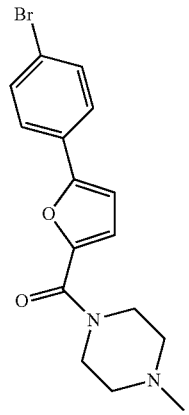

F1040-003

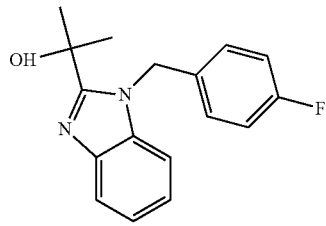

F3287-0507

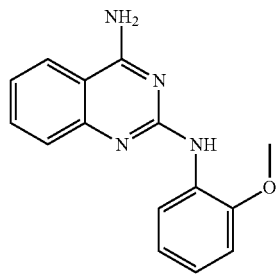

F1684-0555

According to preliminary experiments, these compounds seem to be capable of inhibiting the initial amplification phase of HPV 18.

REFERENCES

1. Bernard H U, Burk R D, Chen Z, van Doorslaer K, zur Hausen H, et al. (2010). Virology 401: 70-79.
2. Humans IWGotEoCRt (2012) Biological agents. Volume 100 B. IARC Monogr Eval Carcinog Risks Hum 100: 1-441.

3. Munoz N, Castellsague X, de Gonzalez A B, Gissmann L (2006) Vaccine 24 Suppl 3: S3/1-10.
4. Munoz N, Bosch F X, de Sanjose S, Herrero R, Castellsague X, et al. (2003) N Engl J Med 348: 518-527.
5. Bouvard V, Baan R, Straif K, Grosse Y, Secretan B, et al. (2009) Lancet Oncol 10: 321-322.
6. Ferlay J, Shin H R, Bray F, Forman D, Mathers C, et al. (2010) E Int J Cancer 127: 2893-2917.
7. Beutner K R, Ferenczy A (1997) Am J Med 102: 28-37.
8. Beutner K R, Tyring S K, Trofatter K F, Jr., Douglas J M, Jr., Spruance S, et al. (1998) Antimicrob Agents Chemother 42: 789-794.
9. Malik H, Khan F H, Ahsan H (2014) Arch Virol 159: 199-205.
10. Roman A, Munger K (2013) Virology 445: 138-168.
11. Vande Pol S B, Klingelhutz A J (2013) Virology 445: 115-137.
12. Doorbar J, Quint W, Banks L, Bravo I G, Stoler M, et al. (2012) Vaccine 30 Suppl 5: F55-70.
13. Hong S, Laimins L A (2013). Future Microbiol 8: 1547-1557.
14. Hebner C M, Laimins L A (2006) Rev Med Virol 16: 83-97.
15. Hughes F J, Romanos M A (1993) Nucleic Acids Res 21: 5817-5823.
16. Clower R V, Fisk J C, Melendy T (2006) P. J Virol 80: 1584-1587.
17. Loo Y M, Melendy T (2004). J Virol 78: 1605-1615.
18. Masterson P J, Stanley M A, Lewis A P, Romanos M A (1998) J Virol 72: 7407-7419.
19. Bergvall M, Melendy T, Archambault J (2013) The E1 proteins. Virology 445: 35-56.
20. McBride A A, Sakakibara N, Stepp W H, Jang M K (2012) Biochim Biophys Acta 1819: 820-825.
21. McBride A A (2013). Virology 445: 57-79.
22. Marechal A, Zou L (2013) Cold Spring Harb Perspect Biol 5.
23. Wang H, Zhang X, Teng L, Legerski R J (2015) D Exp Cell Res.
24. Weitzman M D, Lilley C E, Chaurushiya M S (2010) G Annu Rev Microbiol 64: 61-81.
25. McFadden K, Luftig M A (2013) Curr Top Microbiol Immunol 371: 229-257.
26. Xiaofei E, Kowalik T F (2014) Viruses 6: 2155-2185.
27. Reinson T, Toots M, Kadaja M, Pipitch R, Allik M, et al. (2013) E J Virol 87: 951-964.
28. Moody C A, Laimins L A (2009) PLoS Pathog 5: e1000605.
29. Fradet-Turcotte A, Bergeron-Labrecque F, Moody C A, Lehoux M, Laimins L A, et al. (2011) J Virol 85: 8996-9012.
30. Gillespie K A, Mehta K P, Laimins L A, Moody C A (2012) J Virol 86: 9520-9526.
31. Sakakibara N, Mitra R, McBride A A (2011) J Virol 85: 8981-8995.
32. Anacker D C, Gautam D, Gillespie K A, Chappell W H, Moody C A (2014). J Virol 88: 8528-8544.
33. Mehta K, Gunasekharan V, Satsuka A, Laimins L A (2015) PLoS Pathog 11: e1004763.
34. Kadaja M, Isok-Paas H, Laos T, Ustav E, Ustav M (2009) PLoS Pathog 5: e1000397.
35. Kadaja M, Sumerina A, Verst T, Ojarand M, Ustav E, et al. (2007) EMBO J 26: 2180-2191.
36. Orav M, Henno L, Isok-Paas H, Geimanen J, Ustav M, et al. (2013) J Virol 87: 12051-12068.
37. Pommier Y (2013) ACS Chem Biol 8: 82-95.
38. Interthal H, Pouliot J J, Champoux J J (2001) Proc Natl Acad Sci USA 98: 12009-12014.
39. Murai J, Huang S Y, Das B B, Dexheimer T S, Takeda S, et al. (2012) T J Biol Chem 287: 12848-12857.
40. Das B B, Antony S, Gupta S, Dexheimer T S, Redon C E, et al. (2009) EMBO J 28: 3667-3680.
41. Interthal H, Chen H J, Champoux J J (2005) J Biol Chem 280: 36518-36528.
42. Park S Y, Cheng Y C (2005) Cancer Res 65: 3894-3902.
43. Malanga M, Althaus F R (2004) J Biol Chem 279: 5244-5248.
44. Schreiber V, Dantzer F, Ame J C, de Murcia G (2006) Nat Rev Mol Cell Biol 7: 517-528.
45. Das B B, Huang S Y, Murai J, Rehman I, Ame J C, et al. (2014) Nucleic Acids Res 42: 4435-4449.
46. Pommier Y, Huang S Y, Gao R, Das B B, Murai J, et al. (2014) DNA Repair (Amst) 19: 114-129.
47. Huang S N, Pommier Y, Marchand C (2011) Expert Opin Ther Pat 21: 1285-1292.
48. Geimanen J, Isok-Paas H, Pipitch R, Salk K, Laos T, et al. (2011) D J Virol 85: 3315-3329.
49. Sankovski E, Mannik A, Geimanen J, Ustav E, Ustav M (2014) J Virol 88: 961-973.
50. Toots M, Mannik A, Kivi G, Ustav M, Jr., Ustav E, et al. (2014) PLoS One 9: e116151.
51. Wang X, Meyers C, Wang H K, Chow L T, Zheng Z M (2011) C J Virol 85: 8080-8092.
52. Chow L T, Nasseri M, Wolinsky S M, Broker T R (1987) J Virol 61: 2581-2588.
53. Isok-Paas H, Mannik A, Ustav E, Ustav M (2015) Virol J 12: 59.
54. Kay M A, He C Y, Chen Z Y (2010) Nat Biotechnol 28: 1287-1289.
55. Kirchmaier A L, Sugden B (1995) J Virol 69: 1280-1283.
56. Antony S, Marchand C, Stephen A G, Thibaut L, Agama K K, et al. (2007) N Nucleic Acids Res 35: 4474-4484.
57. Dexheimer T S, Gediya L K, Stephen A G, Weidlich I, Antony S, et al. (2009) 4 J Med Chem 52: 7122-7131.
58. Penning T D, Zhu G D, Gandhi V B, Gong J, Liu X, et al. (2009) J Med Chem 52: 514-523.
59. Wahlberg E, Karlberg T, Kouznetsova E, Markova N, Macchiarulo A, et al. (2012) Nat Biotechnol 30: 283-288.
60. Basu B, Sandhu S K, de Bono J S (2012) Drugs 72: 1579-1590.
61. Chen A (2011) P Chin J Cancer 30: 463-471.
62. Redinbo M R, Stewart L, Kuhn P, Champoux J J, Hol W G (1998) Science 279: 1504-1513.
63. Hsiang Y H, Hertzberg R, Hecht S, Liu L F (1985) C I. J Biol Chem 260: 14873-14878.
64. Lepik D, Ilves I, Kristjuhan A, Maimets T, Ustav M (1998) p J Virol 72: 6822-6831.
65. Yates J L, Guan N (1991) . J Virol 65: 483-488.
66. Archambault J, Melendy T (2013). Antivir Ther 18: 271-283.
67. Mayr L M, Bojanic D (2009) Curr Opin Pharmacol 9: 580-588.
68. Fradet-Turcotte A, Morin G, Lehoux M, Bullock P A, Archambault J (2010) Virology 399: 65-76.
69. Edwards T G, Vidmar T J, Koeller K, Bashkin J K, Fisher C (2013) PLoS One 8: e75406.

What is claimed is:

1. A method to reduce or decrease viral replication in high risk HPV-infection, said method comprising administration of, or contacting infected cells with a compound capable of inhibiting one or more replication phases of Human Papilloma Virus, wherein the compound inhibits release of Topoisomerase I cleaving complex Top1cc from HPV DNA, wherein the compound is selected from the group consisting of:

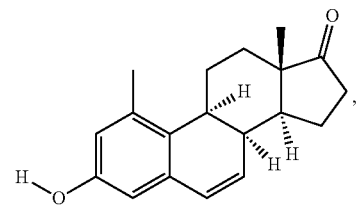

NSC 9782

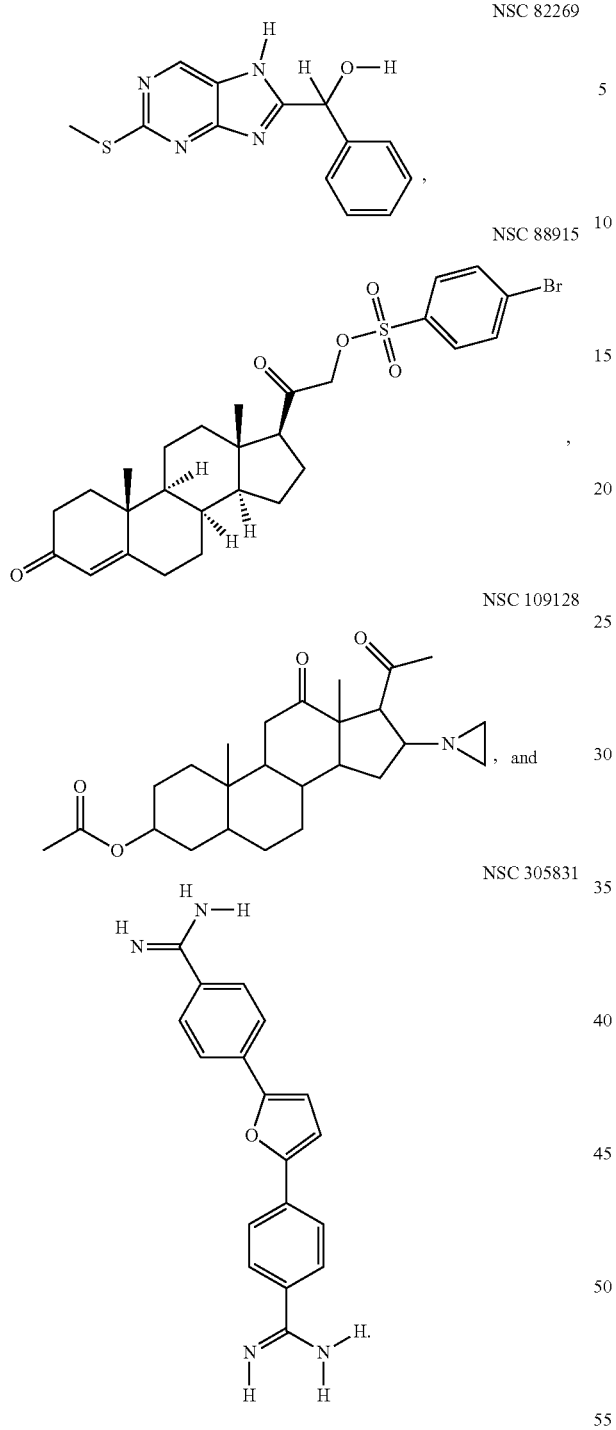

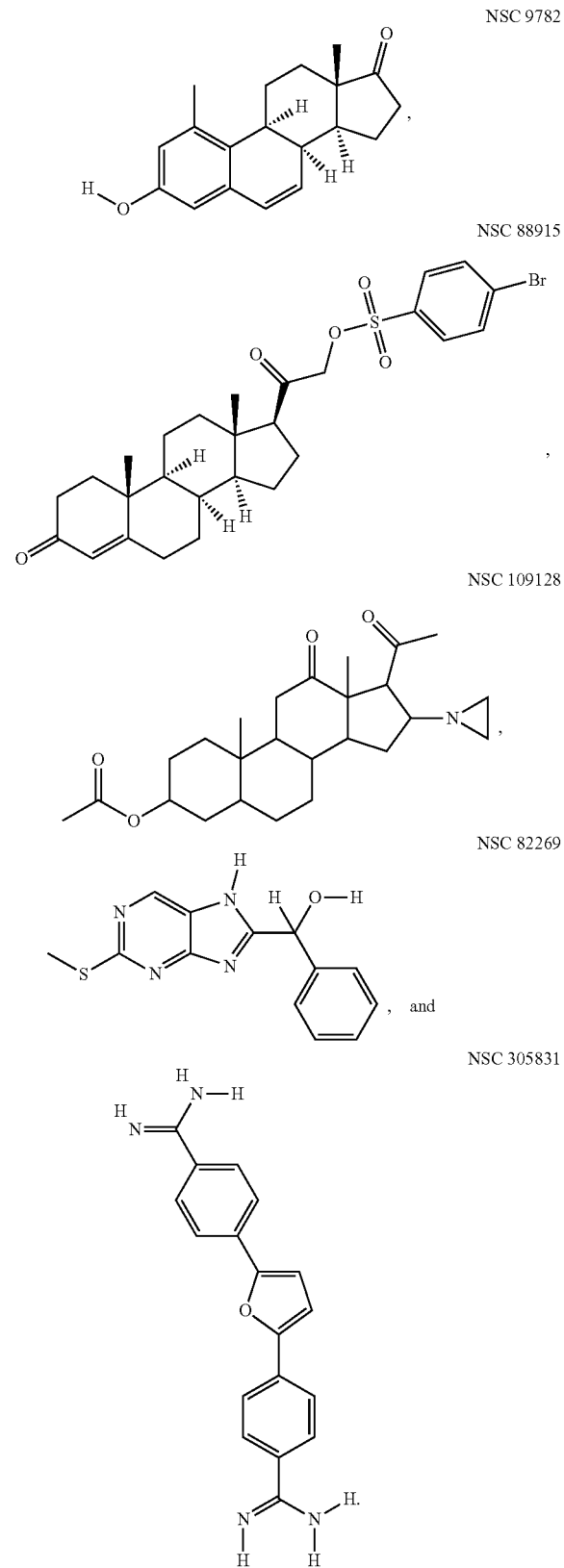

2. The method of claim 1, wherein the release of Topoisomerase I cleaving complex Top1cc from HPV DNA is inhibited by inhibiting Tpd1 or PARP 1.

3. The method of claim claim 1, wherein the HPV is HPV 16, HPV18, HPV31, HPV33 or HPV45.

4. A method to inhibit one or more replication phases of high risk HPV in vitro or in vivo, said method comprising a step of contacting the infected cell with a compound inhibiting release of Topoisomerase I cleaving complex Top1cc from HPV DNA, wherein the compound is selected from the group consisting of:

5. The method of claim 4, wherein the release of Topoisomerase I cleaving complex Top1cc from HPV DNA is inhibited by inhibiting Tpd1 or PARP 1.

6. The method of claim 4, wherein the HPV is HPV 16, HPV 18, HPV31, HPV33 or HPV45.
7. A method to reduce or decrease viral replication in high risk HPV infection, the method comprising a step of administration of, or contacting infected cells with any one of the compounds:
F1040-003
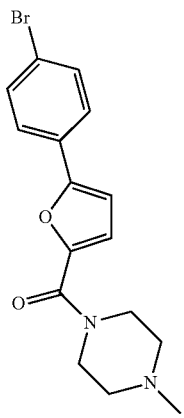
F1684-0555
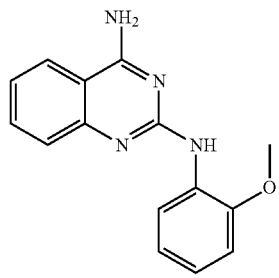
F3287-0507
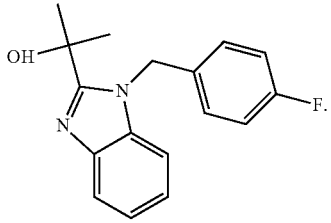
8. The method of claim 7, wherein the HPV is HPV18.
* * * * *